US010569382B2

(12) United States Patent
Beckman et al.

(10) Patent No.: US 10,569,382 B2
(45) Date of Patent: *Feb. 25, 2020

(54) ABRASIVE TOOL INDICATOR SYSTEM, METHOD AND APPARATUS

(71) Applicant: United Technologies Corporation, Hartford, CT (US)

(72) Inventors: Micah Beckman, Middletown, CT (US); David Masiukiewicz, Vernon, CT (US)

(73) Assignee: United Technologies Corporation, Farmington, CT (US)

( * ) Notice: Subject to any disclaimer, the term of this patent is extended or adjusted under 35 U.S.C. 154(b) by 123 days.

This patent is subject to a terminal disclaimer.

(21) Appl. No.: 15/076,793

(22) Filed: Mar. 22, 2016

(65) Prior Publication Data

US 2016/0199960 A1 Jul. 14, 2016

Related U.S. Application Data

(63) Continuation of application No. PCT/US2014/068190, filed on Dec. 2, 2014.

(60) Provisional application No. 61/915,926, filed on Dec. 13, 2013.

(51) Int. Cl.
*B24B 37/005* (2012.01)
*G01N 3/56* (2006.01)

(52) U.S. Cl.
CPC ........... *B24B 37/0053* (2013.01); *G01N 3/56* (2013.01); *G01N 2203/06* (2013.01); *G01N 2203/0605* (2013.01)

(58) Field of Classification Search
USPC ........................ 116/208, DIG. 1; 415/118, 9; 188/1.11 R, 1.11 W; 73/86
See application file for complete search history.

(56) References Cited

U.S. PATENT DOCUMENTS

| 4,447,992 A * | 5/1984 | Bergquist ................ B24B 41/06 |
| | | 451/29 |
| 6,513,370 B1 | 2/2003 | Williams |
| 2011/0047777 A1* | 3/2011 | Soucy ..................... B24B 31/00 |
| | | 29/525.01 |
| 2011/0296687 A1 | 12/2011 | Hebuterne et al. |
| 2011/0311389 A1 | 12/2011 | Ryan et al. |
| 2012/0285226 A1 | 11/2012 | Laurer et al. |

(Continued)

FOREIGN PATENT DOCUMENTS

WO WO2007139473 * 12/2007 ............. A47L 15/02

OTHER PUBLICATIONS

International Search Report and Written Opinion dated Apr. 14, 2015 in Application No. PCT/US2014/068190.

(Continued)

*Primary Examiner* — Brian D Keller
(74) *Attorney, Agent, or Firm* — Snell & Wilmer, L.L.P.

(57) ABSTRACT

A tool comprising a plurality of wear indicators is provided. The tool may be made from a rapid prototyping process. The tool may be used in an abrasive processing operation. The tool may comprise one or more control elements, (e.g., control geometries, part interfaces, fixture interfaces and/or the like). These control elements may comprise indicators of tool wear. The indicators may be inspected physically (e.g., by touch) and/or visually.

14 Claims, 5 Drawing Sheets

(56) References Cited

U.S. PATENT DOCUMENTS

2012/0302145 A1* 11/2012 Bitter .................. G02B 6/3863
451/364

OTHER PUBLICATIONS

International Preliminary Report on Patentability dated Jun. 14, 2016 in Application No. PCT/US2014/068190.

* cited by examiner

ABRASIVE TOOL INDICATOR SYSTEM, METHOD AND APPARATUS

CROSS-REFERENCE TO RELATED APPLICATIONS

This application is a continuation of, claims priority to and the benefit of, PCT/US2014/068190 filed on Dec. 2, 2014 and entitled "ABRASIVE TOOL INDICATOR SYSTEM, METHOD AND APPARATUS," which claims priority from U.S. Provisional Application No. 61/915,926 filed on Dec. 13, 2013 and entitled "ABRASIVE TOOL INDICATOR SYSTEM, METHOD AND APPARATUS." Both of the aforementioned applications are incorporated herein by reference in their entirety.

FIELD

The present disclosure relates to wear indicators for tooling, and more specifically, wear indicators for rapidly prototyped tooling used in abrasive processing.

BACKGROUND

Tools produced through rapid prototyping such as, for example, stereo-lithography and/or the like may be used in abrasive processes and may be designed to fit to a part being worked. These tools may include controlled geometry elements, interface surfaces, and other specifically controlled geometries. These tooling elements may be considered to be worn out when they no longer fit the particular part being worked and/or one or more of the controlled geometry elements has eroded to a sufficient level. These elements may need continuous inspection and/or to be frequently measured to ensure that the geometries that control and define the controlled geometry elements and/or the locations of the tools specified elements meet design specifications. These measurements and/or inspections may be costly and generally inefficient.

SUMMARY

In various embodiments, a tool may comprise a body and a geometric feature. The geometric feature may be integrally formed on the body. The geometric feature may comprise a first surface comprising a plurality of wear indicators. The plurality of wear indicators may be configured to indicate varying degrees of tool erosion.

A wear monitoring system comprising a tool is provided. The tool may comprise a body and a control geometry. The body may be configured to receive and retain a part to be worked in an abrasive process. The control geometry may be associated with a feature of the part to be worked. The control geometry may comprise a plurality of wear indicators configured to indicate varying degrees of tool wear.

A method for inspecting abrasive process tooling is provided. The method may comprise: identifying an inspection location of a tool, the inspection location comprising a plurality of indicators; comparing a first indicator of the plurality of indicators to a standard; and determining the status of the tool based on at least one of the first indicator and the standard.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the inventions, it should be understood that other embodiments may be realized and that logical, chemical and mechanical changes may be made without departing from the spirit and scope of the disclosure. Thus, the detailed description herein is presented for purposes of illustration only and not of limitation. For example, the steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

As used herein, phrases such as "make contact with," "coupled to," "touch," "interface with" and "engage" may be used interchangeably. Different surface shading may be used throughout the figures to denote different parts but not necessarily to denote the same or different materials.

In various embodiments, aerospace parts such as stators and other precisely manufactured devices may require specialized finishing processes, including, for example, abrasive finishing, precision grinding and/or the like. These processes may involve immersion or contact with abrasive materials. The aerospace parts may be installed in specially designed tools. These tools may contact the abrasive material and/or process while the tool is being processed. The tools may wear and/or wear out without any indication of when the tool is no longer suitable and/or effective for processing of the aerospace part. As such, these tools may require calibration and/or regular inspection. This inspection process may not be cost effective and/or efficient. For example, the tools may require inspection that takes the tool out of service and/or limits production capacity while the tool is being inspected. Moreover, tools may be constructed with controlled geometry surfaces that affect the finishing process(es). For example, where a tool is used to process a stator, the tool may be designed with deliberate functions, such as controlled geometry elements (e.g., mock airfoils) and/or the like. In this example of the controlled geometry features, the mock air foils may protect the air foils and control the effect of the abrasive process on the air foils at the ends of the stator segment, replicating the stator operational environment where a stator assembly and associated neighboring stator blades would be present. These mock air foils are controlled surfaces that would require continuous or systematic inspection.

The addition of one or more wear indicators and/or inclusions allows the geometry of the control surfaces to be easily checked and/or inspected. For example, an operator may visually or manually inspect a controlled geometry surface to determine whether a wear indicator and/or inclusion can be seen or felt. In this regard, visual and/or physical inspection may be suitable to replace more traditional measurement inspection, providing a more cost effective and time efficient evaluation process for rapidly prototyped tooling used in abrasive processes.

Figure 1:
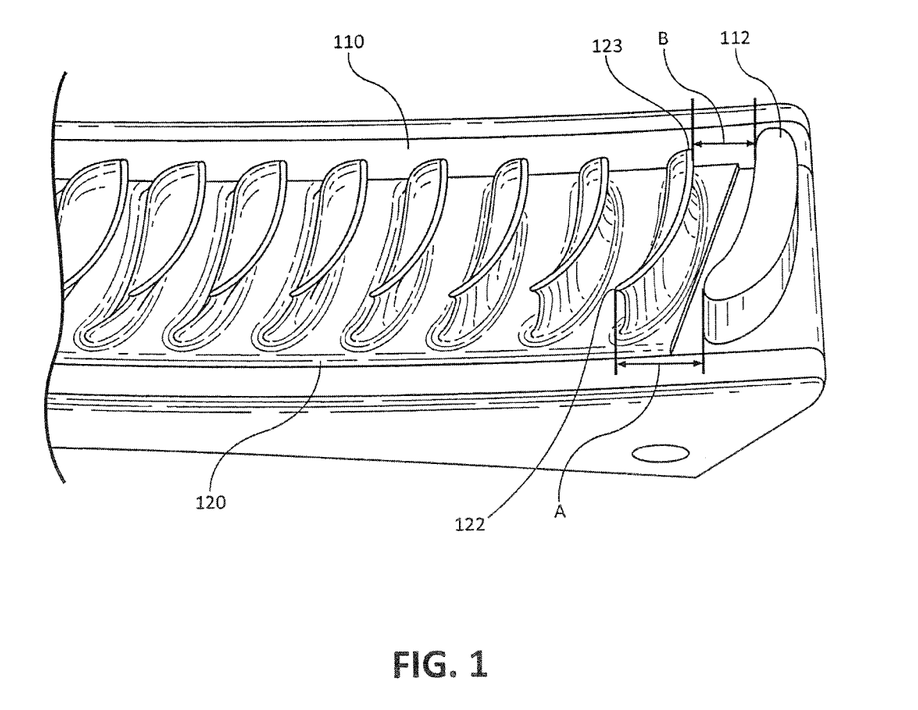
FIG. 1 illustrates a partial perspective view of a tool comprising a part to be worked, in accordance with various embodiments.

In various embodiments and with reference to FIG. 1, a tool 110 (e.g., a body portion, a body, a housing, and/or the like) may comprise a control geometry 112. Tool 110 may further comprise and/or define a channel configured to receive and hold a part to be worked 120. In this regard, the channel may be configured to couple to and/or receive a part to be worked 120 (e.g., a portion of a stator assembly). One or more control geometry 112 may interact with part 120 and/or the abrasive media in an abrasive process to control the effect of an abrasive media on the part. In this regard, control geometry 112 may insure that the abrasive effect of part processing on part 120 is consistent from part to part (e.g., a first part 120 is processed substantially similarly to a second part 120, where processed substantially similarly means that first part 120 is equivalent to second part 120 within an acceptable geometric tolerance. For example, where part 120 is a stator comprising a plurality of airfoils, control geometry 112 may be a mock airfoil. In this regard, the mock airfoil may include (1) a first surface that may be a distance "A" from a first surface 122 of one of the plurality of airfoils of part 120 and (2) a second surface 123 that may be a distance "B" from a second surface of one of the plurality of airfoils of part 120. Tool 110 and/or the included mock airfoil may be configured to protect and/or control the abrasive effect of the abrasive media on an airfoil at an end of part 120.

In various embodiments, tool 110 may be made of a material that is appropriate for rapid prototyping. For example, tool 110 may be made from sintered powder. In various embodiments, tool 110 may be made from a laser sintering process. This process may include a laser that interacts with a sintered powder to melt the powder into a defined tool geometry. The laser may heat and solidify portions or particular geometries in the sintered powder.

Figure 2A:
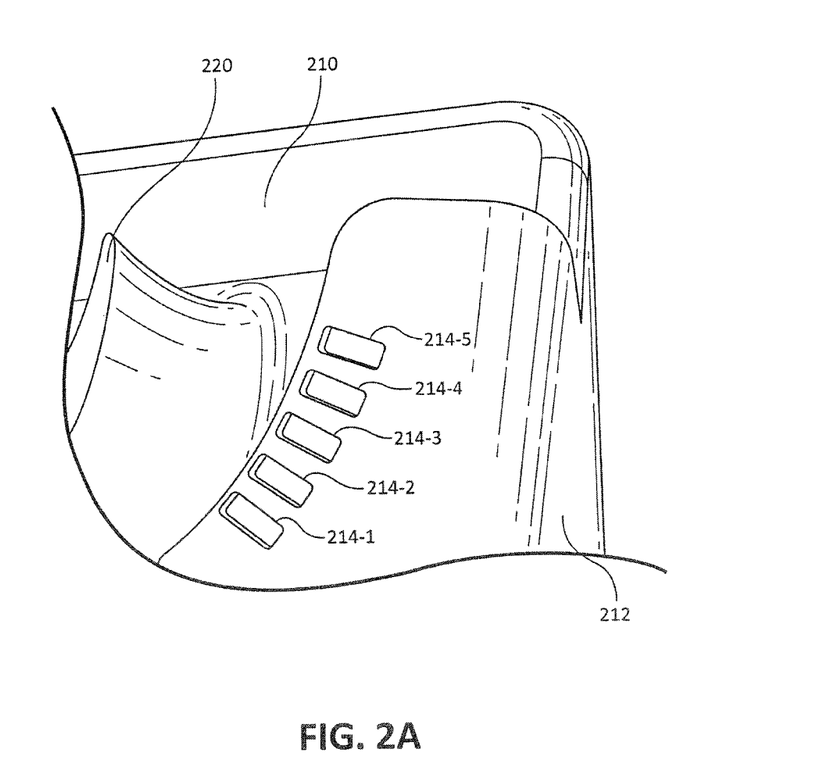
FIG. 2A illustrates a perspective view of a portion of a tool comprising a part to be worked and a controlled geometry comprising a first series of exposed wear indicator, in accordance with various embodiments.

In various embodiments and with reference to FIG. 2A, control geometry 212 such as, for example, a mock airfoil may be manufactured at a specific location in tool 210 using a laser sintering process. The location and/or position of control geometry 212 may be defined by the resolution of the laser. In this regard, the location and/or shape may be designed such that the resolution of the laser is capable of obtaining that position and/or shape. More specifically, these control geometry 212 (e.g., mock air foils) may be located in positions and are shaped such that they act as neighboring air foils to the air foils at the end of each segment in part 220 (e.g., a stator).

In various embodiments, tool 210 may comprise a control geometry 212 with a plurality of wear indicators 214 (shown as wear indicator 214-1, wear indicator 214-2, wear indicator 214-3, wear indicator 214-4, and/or wear indicator 214-5 in FIG. 2A). Moreover, tool 210 may comprise any suitable number of wear indicators 214. The controlled geometry surface may be any suitable interface between tool 210 and part 220, a fixture, a processing element (e.g., a machine), an inspection element (e.g. an inspection interface), and/or the like.

Figure 2B:
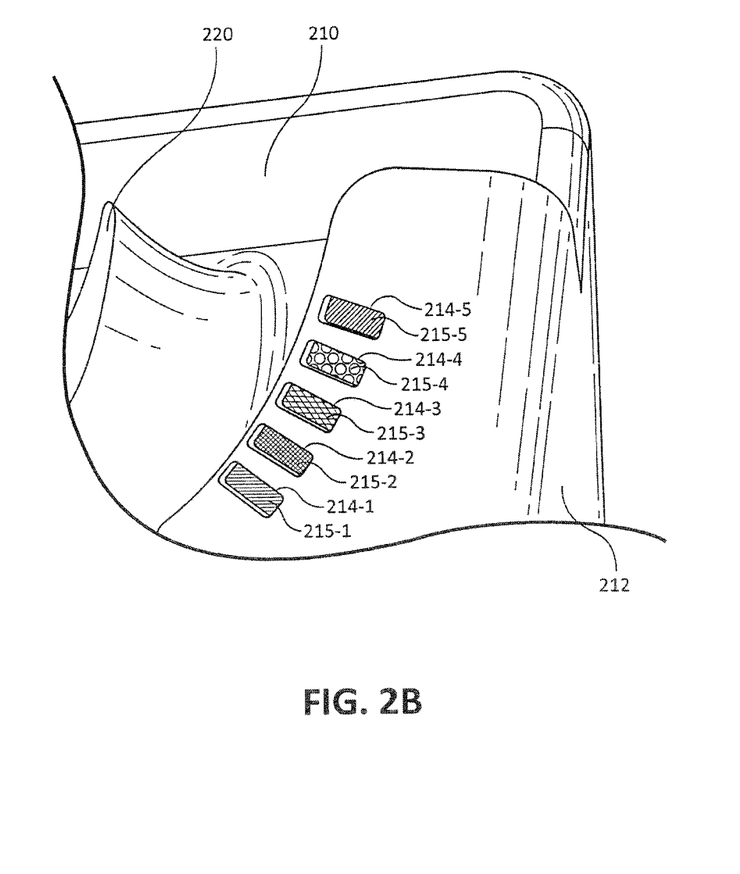
FIG. 2B illustrates a perspective view of a portion of a tool comprising a part to be worked and a controlled geometry comprising a second series of exposed wear indicator, in accordance with various embodiments.

In various embodiments and with reference to FIG. 2B, the plurality of wear indicator 214 may be configured to display degrees of wear. For example, one or more wear indicators 214 may be configured with detectable wear identifiers 215 (shown as identifier 215-1, identifier 215-2, identifier 215-3, identifier 215-4, and identifier 215-5). Identifier 215 may include various colors. For example, identifier 215-1 may comprise a color indicator preliminary wear (e.g., green). In this regard, wear may be exhibited on a control geometry 212 of tool 210, but no immediate action is required. Identifier 215-3 may comprise a color indicator indicating intermediate wear (e.g., yellow). In this regard, wear may be exhibited on control geometry 212 of tool 210 indicated that a replacement tool should be ordered based on a known lead-time for the tool, a projected production requirement, an operational and/or logistics requirement and/or the like. Identifier 215-5 may comprise a color indicator indicating tool replacement (e.g., red). In this regard, wear may be sufficient on control geometry 212 of tool 210 to expect and/or exhibit out of tolerance processing properties, indicating and/or necessitating that tool 210 be replaced to insure proper processing of part to be worked 220.

In various embodiments, tool 210 may also include intermediate identifiers 215 (shown as identifier 215-2 and identifier 215-4 in FIG. 2B). Intermediate identifiers 215 may be configured to identify other quantifiable attributes of tool 210 including for example, number of parts 220 processed, volume of abrasive media used, and/or the like.

In various embodiments, one or more indicators 214 may comprise a secondary identifier 215 (e.g., a powder) that acts as a second visual indicator. Secondary identifier 215 may be a powder that is added to indicator 214 when tool 210 is being manufactured. Secondary identifier 215 may also be an un-sintered and/or un-melted powder that is retained within indicator 214 from tool 210 manufacturing. In this regard, the indicator may house, contain, and/or include secondary identifier 215. For example, when tool 210 wears to a point that one or more indicator 214 are opened and/or exposed, secondary identifiers 215 may spill out of indicators 214 such that secondary identifiers 215 acts as a second indicator that indicator 214 is exposed and/or that tool 210 is sufficiently worn to need replacement.

Figure 3:
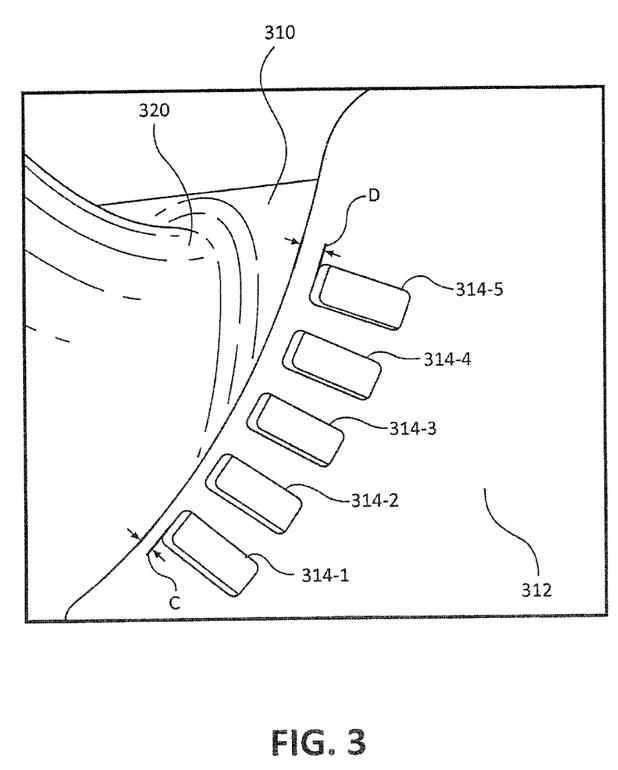
FIG. 3 illustrates a perspective view of a portion of a tool comprising a part to be worked and a plurality of graduated exposed wear indicators, in accordance with various embodiments.

In various embodiments and with reference to FIG. 3, indictors 314 formed in control geometry 312 may be spaced at varying longitudinal distances from an edge of control surface of control geometry 312. In this regard, the control surface may be a surface that is longitudinally closest too and/or adjacent a portion of part to be worked 320. For example, a first indicator 314-1 may be a first longitudinal distance "C" from an interior control surface of control geometry 312. A fifth indicator 314-5 may be a fifth longitudinal distance "D" from the interior control surface of control geometry 312. Each of the intermediate indicators 313 (e.g., 314-2, 314-3, and 314-4) may be proportionally further distance away from the interior control surface of control geometry 312. In this regard, each of the indicators 314 may be capable of and/or configured to be exposed in response to a predetermined amount of wear. In this regard, tool 310 may be evaluated, reorder, inspected and/or the like by visual and/or tactile inspection to determine whether reorder and/or replacement of the tool is necessary.

Figure 4:
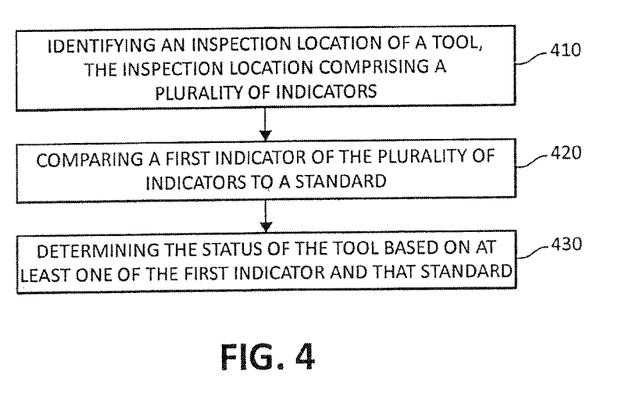
FIG. 4 illustrates a method for tool inspection, in accordance with various embodiments.

In various embodiments and with reference to FIG. 4, a method of inspecting a tool used in an abrasive process may be provided. During inspection of a tool (e.g., tool 110 as discussed herein and as shown in FIG. 1), an inspection location of a tool is identified (Step 410). The inspection location may comprise a plurality of indicators. A first indicator of the plurality of indicators may be compared to a standard (Step 420). The first indicator may be visually and/or physically evaluated (e.g., by touch). In this regard, the standard may provide for an appropriate action by an inspector based on the detected wear and/or life of the tool. For example, the first indicator may include a color indicator and/or other secondary indicator as discussed herein. When evaluated against a standard, the color and/or secondary indicator may indicate that the tool has experienced sufficient wear that a replacement tool should be ordered. The standard may be established by a tool manufacturer, tool user, and/or the like. The standard may be based on expected tool life, quality control standards, and/or the like. Based on the first indicator and/or the standard, the status of the tool may be determined (Step 430). In this regard, the standard, the color indicator, and/or the secondary indicator may also indicate whether a tool can be returned to service or should be discarded. The inspection method shown in FIG. 4 and described herein may make use of any of the tools, indicators, secondary indicators, parts and/or features disclosed herein.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

What is claimed is:

1. A tool configured to hold a part to be worked, the tool comprising:
    a body comprising a channel configured to receive and hold the part, the part comprising a plurality of airfoils; and
    a mock airfoil integrally formed on an end of the body, the mock airfoil comprising a convex surface, a concave surface opposing the convex surface, and a plurality of wear indicators, the plurality of wear indicators configured to indicate varying degrees of tool erosion, wherein a controlled geometry surface of the mock airfoil is either the convex surface or the concave surface;
    wherein the controlled geometry surface of the mock airfoil is configured to allow and control an abrasive effect of an abrasive process on a surface of an end airfoil of the plurality of airfoils of the part that faces, and is adjacent to, the controlled geometry surface of the mock airfoil,
    wherein the controlled geometry surface of the mock airfoil is shaped to resemble the surface of the end airfoil such that the mock airfoil is configured to replicate an operational environment where a neighboring airfoil of a neighboring plurality of airfoils would be present.

2. The tool of claim 1, wherein the plurality of wear indicators comprises a first wear indicator, a second wear indicator, and a third wear indicator.

3. The tool of claim 2, wherein the first wear indicator comprises a color indicator.

4. The tool of claim 2, wherein the first wear indicator comprises a secondary indicator.

5. The tool of claim 4, wherein the secondary indicator is a powder, wherein the first wear indicator is a housing that retains the powder, wherein the housing is configured to open and the powder is configured to spill out the housing in response to wear.

6. The tool of claim 5, wherein the tool is made from a rapid prototyping process.

7. The tool of claim 1, wherein the mock airfoil is configured to be disposed a distance away from the end airfoil such that a gap is defined between the controlled geometry surface of the mock airfoil and the surface of the end airfoil facing the controlled geometry surface, wherein abrasive media of the abrasive process passes through the gap and affects the surface of the end airfoil.

8. The tool of claim 7, wherein the distance is a uniform distance between adjacent airfoils of the plurality of airfoils.

9. The tool of claim 1, wherein the controlled geometry surface of the mock airfoil replicates the end airfoil, and also replicates a corresponding surface of individual airfoils of the plurality of airfoils.

10. A wear monitoring system, comprising:
a tool configured to hold a part to be worked, the tool comprising,
a body defining a channel configured to receive and retain the part to be manufactured in an abrasive process, wherein the part comprises a plurality of airfoils, and
a structure integrally formed on an end the body of the tool, the structure comprising a convex surface, a concave surface opposing the convex surface, and a plurality of wear indicators configured to indicate varying degrees of tool wear, wherein either the convex surface or the concave surface is a control geometry;
wherein the control geometry is configured to face a surface of an end airfoil of the plurality of airfoils such that the control geometry is configured to allow and control an abrasive effect of the abrasive process on the surface of the end airfoil of the plurality of airfoils, wherein the control geometry is shaped to resemble the surface of the end airfoil such that the control geometry is configured to replicate an operational environment where a neighboring airfoil of a neighboring plurality of airfoils would be present.

11. The wear monitoring system of claim 10, wherein each of the plurality of indicators comprises a secondary indicator, wherein the secondary indicator is a powder, wherein each of the plurality of indicators is a housing that retains the powder, wherein the housing of each of the plurality of indicators is configured to open and the powder is configured to spill out the housing of each of the plurality of indicators in response to wear, wherein the secondary indicator is a color indicator.

12. The wear monitoring system of claim 11, wherein the secondary indicator is a first secondary indicator, wherein the plurality of indicators further comprises a second secondary indicator.

13. The wear monitoring system of claim 10, wherein a first indicator of the plurality of indicators is a first distance from an edge of the control geometry and a second indicator of the plurality of indicators is a second distance from the edge of the control geometry.

14. The wear monitoring system of claim 10, wherein the plurality of indicators comprises a first indicator, a second indicator, and a third indicator.

* * * * *